(12) United States Patent
Driessen-Hölscher et al.

(10) Patent No.: US 6,462,200 B2
(45) Date of Patent: Oct. 8, 2002

(54) DIPHOSPHINES

(75) Inventors: Birgit Driessen-Hölscher, Aachen; Joachim Kralik, Darmstadt; Inga Ritzkopf; Christian Steffens, both of Aachen; Guido Giffels, Bonn; Claus Dreisbach, Köln; Thomas Prinz, Leverkusen; Walter Lange, Odenthal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/948,826

(22) Filed: Sep. 7, 2001

(65) Prior Publication Data

US 2002/0055653 A1 May 9, 2002

(30) Foreign Application Priority Data

Sep. 11, 2000 (DE) .......................... 100 44 793

(51) Int. Cl.⁷ .......................... C07F 9/572; C07F 9/655; C07F 9/50
(52) U.S. Cl. .......................... 548/412; 549/216; 568/13
(58) Field of Search .......................... 549/219; 548/412; 568/13, 16, 17

(56) References Cited

U.S. PATENT DOCUMENTS

| 4,556,740 A | 12/1985 | Hansen et al. ................. 568/13 |
| 5,508,438 A | 4/1996 | Broger et al. ................... 549/6 |
| 5,621,128 A | 4/1997 | Jendralla ....................... 556/18 |
| 5,710,339 A | 1/1998 | Laue et al. .................... 568/16 |
| 5,801,261 A | 9/1998 | Laue et al. .................... 556/16 |
| 5,847,222 A * | 12/1998 | Yokozawa et al. ............ 568/16 |

OTHER PUBLICATIONS

Tetrahedron Lett., 36, (month unavailable) 1995, pp. 7991–7994, Dongwei Cai, David L. Hughes, Thomas R. Verhoeven, and Pual J Reider, Simple and Efficient Resoltion of 1,1–Bik–2–naphthol.

* cited by examiner

Primary Examiner—Jean F. Vollano
(74) Attorney, Agent, or Firm—Joseph C. Gil; Richard E.L. Henderson; Godfried R. Akorli

(57) ABSTRACT

The invention relates to the preparation and use as catalysts of diphosphines of the formula (I)

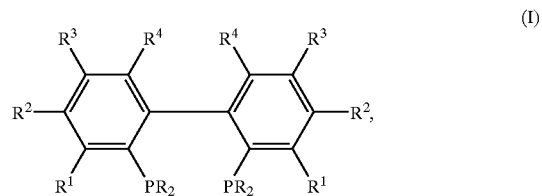

in which

R is $C_{6-C_{14}}$-aryl or $C_{4-C_{13}}$-heteroaryl containing 1 to 3 heteroatoms selected from the group consisting of nitrogen, oxygen, and sulfur, wherein the aryl and heteroaryl radicals may optionally be substituted by halogen, $C_{1-C_6}$-alkyl, $C_{1-C_6}$-alkoxy, and/or trimethylsilyl, and $R^1$ to $R^4$, independently of one another, are each hydrogen, $C_{1-C_{10}}$-alkyl, $C_{1-C_{10}}$-alkoxy, F, Cl, or Br.

1 Claim, No Drawings

DIPHOSPHINES

BACKGROUND OF THE INVENTION

The present invention relates to a process for the preparation of racemic diphosphines, to a process for the preparation of enantiomerically pure diphosphines, to novel enantiomerically pure diphosphines, to novel intermediates for the preparation of diphosphines, and to catalysts that contain novel diphosphines.

A process that differs greatly from the process according to the invention for the preparation of diphosphines is known from EP-A 749,973. According to this, if the intention is to prepare enantiomerically pure diphosphines, the racemate resolution is carried out at the stage of the phosphine oxides, i.e., for individual diphosphines separate racemate resolutions must be carried out. Compounds different from the compounds according to the invention are described in EP-A 104,375, EP-A 582,692, and EP-A 690,065. Racemate resolutions with N-benzylcinchonidinium chloride have hitherto been described only for dinaphthol compounds (Tetrahedron Lett. 36, 7991 (1995)).

SUMMARY OF THE INVENTION

Specifically, the present invention first relates to a process for the preparation of racemic diphosphines of the formula (I)

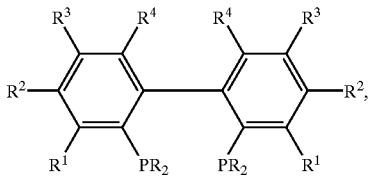

in which

R is $C_6–C_{14}$-aryl or $C_4–C_{13}$-heteroaryl containing 1 to 3 heteroatoms selected from the group consisting of nitrogen, oxygen, and sulfur, wherein the aryl and heteroaryl radicals may optionally be substituted by halogen, $C_1–C_6$-alkyl, $C_1–C_6$-alkoxy, and/or trimethylsilyl, and $R^1$ to $R^4$, independently of one another, are each hydrogen, $C_1–C_{10}$-alkyl, $C_1–C_{10}$-alkoxy, F, Cl, or Br, comprising (a) converting a phenol of the formula (II)

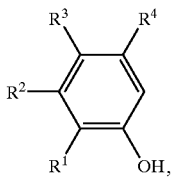

in which $R^1$ to $R^4$ have the meanings given for formula (I), into the corresponding phenoxide using a base, (b) reacting the phenoxide with dihalogenomethane to give a formaldehyde acetal of the formula (III)

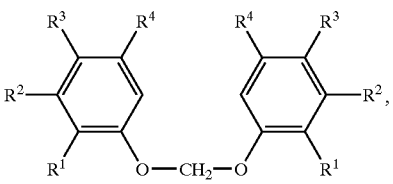

in which $R^1$ to $R^4$ have the meanings given for formula (I), (c) intramolecularly oxidatively coupling the formaldehyde acetal of the formula (III) to give a cycloheptadiene of the formula (IV),

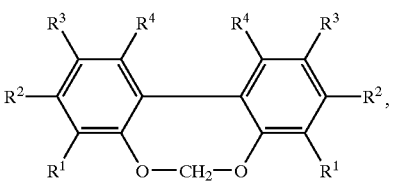

in which $R^1$ to $R^4$ have the meanings given for formula (I), (d) converting the cycloheptadiene of the formula (IV) by treatment with an acid into a biphenyldiol of the formula (V)

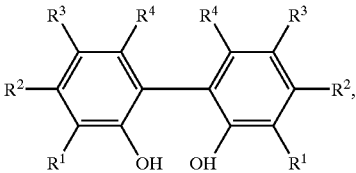

in which $R^1$ to $R^4$ have the meanings given for formula (I), (e) preparing the corresponding triflate from the biphenyldiol of the formula (V), and (f) coupling the triflate with a secondary phosphine of the formula (VI)

$$HPR_2 \quad (VI),$$

in which R has the meaning given for formula (I), with the addition of a base and in the presence of a palladium(0), palladium(II), nickel(0), and/or Ni(II) compound, thereby giving a compound of the formula (I).

DETAILED DESCRIPTION OF THE INVENTION

In the formulas (I) to (V), $R^1$ and $R^2$ are preferably hydrogen and $R^3$ and $R^4$ are preferably $C_1–C_5$-alkoxy, fluorine, or chlorine. In the formulas (I) and (VI), R is preferably phenyl, furyl, or 2-N-$C_1$-$C_6$-alkylpyrrolyl that may optionally be substituted by 1 to 3 substituents from the group consisting of fluorine, chlorine, $C_1–C_5$-alkyl, $C_1–C_6$-alkoxy, and trimethylsilyl. In the formulas (I) to (V), $R^1$ and $R^2$ are particularly preferably hydrogen, $R^3$ is particularly preferably chlorine, and $R^4$ is particularly preferably methoxy or ethoxy. In the formulas (I) and (VI), R is particularly preferably phenyl, 2-furyl, 2-N-methylpyrrolyl, 3,5-dimethylphenyl, 4-fluorophenyl, 4-tolyl, or 3,5-dimethoxyphenyl.

In the conversion of the phenol of the formula (II) into the corresponding phenoxide, the base that can be used is, for example, an alkali metal hydride, hydroxide, or carbonate. Preference is given to sodium hydride and potassium hydride. The base is preferably used in an amount of from 0.9 to 1.5 equivalents per mole of phenol of the formula (II). Here, it is possible to work in the presence of a solvent, e.g., in the presence of a dipolar-aprotic solvent, such as dimethylformamide, or an ether, such as diethyl ether, tetrahydrofuran, dioxane, or methyl tert-butyl ether.

Suitable reaction temperatures, particularly when alkali metal hydrides are used as base, are, for example, those in the range from −20 to +60° C. It is advantageous to carry out this stage under a protective gas atmosphere. The procedure may involve, for example, initially introducing the base together with the solvent and metering in the phenol of the formula (II) dissolved in the same solvent.

The phenoxide obtained does not need to be isolated. Particularly if the process has been carried out with stoichiometric amounts of alkali metal hydride as base, the reaction mixture that is present following reaction with the base can be further used directly.

In the reaction with the phenoxide it is possible to use, based on one mole of phenol of the formula (II) originally used, e.g., 0.4 to 0.7 mol of dihalogenomethane. Suitable reaction temperatures are, for example, those from 0 to 80° C., particularly those from 10 to 60° C. The reaction time for the reaction with the dihalogenomethane can be, for example, 8 to 40 hours. Suitable as dihalogenomethane is, for example, dichloromethane, dibromomethane, and diiodomethane. Diiodomethane is preferred.

The reaction mixture that is then present can be worked up, for example, by extracting it after addition of water with a virtually nonpolar or nonpolar organic solvent and removing the solvent from the extract. The residue that remains can, if desired, be further purified, for example, by dissolving it in an ether, in methanol, or in acetonitrile at elevated temperature, discarding the insoluble components, and obtaining the prepared formaldehyde acetal of the formula (III) in purified form by crystallization.

The intramolecular oxidative coupling for the preparation of a cycloheptadiene of the formula (IV) can be carried out, for example, by first adding an organolithium compound to the formaldehyde acetal of the formula (III) and, when they have finished reacting, adding an oxidizing agent. For example, it is possible to add butyllithium dissolved in, for example, a hydrocarbon to a solution of the formaldehyde acetal, for example in ether, at −30 to +40° C. and leave the mixture to fully react by after-stirring at a temperature in this range. Per mole of formaldehyde acetal, it is possible to use, for example, 2.0 to 2.2 mol of organolithium compound. In general, the reaction is complete after 5 to 30 hours. The oxidizing agent can then be added, for example a Cu(II), Fe(III), Mn(III), or Ce(IV) compound. The oxidative coupling can also be carried out enzymatically, e.g., with a peroxidase. The oxidizing agent is added at, for example, −70 to −30° C., and the mixture is subsequently warmed to a temperature of, for example, below 50° C. Based on 1 mol of formaldehyde acetal of the formula (III) used, it is possible to use, for example, 2.0 to 2.5 equivalents of an oxidizing agent. It is advantageous to continue to after-stir the reaction mixture in conclusion, e.g., for 1 to 5 hours.

It is also possible to carry out the oxidative coupling directly from the formaldehyde acetal of the formula (III) in accordance with the methods described here without converting said formaldehyde acetal into the Li salt beforehand.

It is advantageous at least to carry out the reaction with the organolithium compound under a protective gas atmosphere.

The treatment with an acid to convert a cycloheptadiene of the formula (IV) into a biphenyldiol of the formula (V) can be carried out, for example, with a strong mineral acid such as hydrochloric acid or sulfuric acid. For example, 5 to 15 equivalents of acid can be used per mole of cycloheptadiene of the formula (IV). The procedure is expediently carried out in the presence of a solvent, for example in the presence of an alcohol. The treatment with the acid can be carried out, for example, in a period of from 5 to 50 hours at temperatures of from 50 to 100° C. The reaction mixture can be worked up, for example, analogously to the procedure described above for the preparation of formaldehyde acetals of the formula (III).

The preparation of the triflate compound (i.e., a trifluoromethanesulfonic ester) from the biphenyldiol of the formula (V) can be carried out, for example, by suspending the biphenyldiol of the formula (V) in a solvent (e.g., an aromatic hydrocarbon), adding a tertiary amine (e.g. pyridine), and then metering in, for example, trifluoromethanesulfonic anhydride or trifluoromethanesulfonyl chloride, optionally dissolved in a solvent (e.g., in an aromatic hydrocarbon), and after-stirring. The metered addition and after-stirring can be carried out, for example, at 0 to 60° C. A suspension forms during this operation. Per mole of biphenyldiol of the formula (V), it is possible to use, for example, 2 to 3 mol of a tertiary amine and 2 to 2.2 mol of trifluoromethanesulfonic anhydride or trifluoromethanesulfonyl chloride.

For work-up, the reaction mixture can, for example, be washed with water and aqueous sodium chloride solution, the organic phase that is left behind can be dried, and the solvent can be removed, where necessary by stripping it off under reduced pressure. The product obtainable in this way is pure enough for the reaction with secondary phosphines. If desired, it can be further purified, e.g., by (flash) column chromatography.

For the reaction of the triflate compound with a secondary phosphine of the formula (VI), the base that may be used is, for example, a tertiary amine (for example, a trialkylamine), that contains three identical or different $C_1$–$C_6$-alkyl groups. Arylalkylamines, DABCO, "proton sponges" (e.g. 1,8-bis (dimethylamino)naphthalene) and hydrogen carbonates, such as sodium hydrogen carbonate, are also possible. Preference is given to using triethylamine or ethyldiisopropyl-amine. The amount of base used, based on one mole of the triflate compound, can, for example, be 2 to 3 mol.

Suitable palladium(0) or nickel(0) compounds are, for example complexes of the formulas (VIIa) and (VIIb),

$$Pd(PR'_3)_4 \qquad (VIIa)$$

$$Ni(PR'_3)_4 \qquad (VIIb)$$

in which
R' is in each case $C_1$–$C_{10}$-alkyl or $C_6$–$C_{14}$-aryl, where aryl may optionally be substituted by halogen and/or $C_1$–$C_6$-alkyl, and where R' is preferably phenyl.

Also suitable as palladium(0) compound is $Pd_2(dba)_3$, where dba is dibenzylideneacetone. The $Pd_2(dba)_3$ can optionally also contain a coordinated solvent molecule, e.g., $CHCl_3$.

It is also possible to use a palladium(0) compound of the formula (VIIc)

$$Pd(L_2) \qquad (VIIc),$$

in which

L is R'$_2$P—(CH$_2$)$_n$—PR'$_2$, diphenylphosphinoferrocenyl, or 2,2'-bis(diphenylphosphinomethyl)-1,1'-binaphthyl, where R' has the meaning given above and n is 1, 2, 3, or 4.

Preferred compounds of the formula (VIIc) are those in which L is R'$_2$P—(CH$_2$)$_n$—PR'$_2$, where R' is phenyl and n is 2, 3, or 4.

Suitable as palladium(II) compound is, for example, Pd(CH$_3$COO)$_2$, and suitable as nickel(II) compound, for example, NiCl$_2$ that optionally also contains 1 to 2 coordinated PR'$_3$-molecules (where R' has the same meaning as in the formulas (VIIa) and (VIIb)).

Preference is given to using palladium(0) compounds of the formulas (VIIa) and (VIIc) and Pd$_2$(dba)$_3$. These compounds can, if desired, also be prepared in situ, for example, by initially introducing palladium diacetate into a solvent and adding the ligands in the stoichiometrically required amount or in an excess of up to, for example, 150% of the stoichiometrically required amount.

The amount of palladium and/or nickel compounds used, based on 1 mol of triflate compound, can be, for example, 0.001 to 0.1 mol.

The reaction of the triflate compound with a secondary phosphine of the formula (VI) can be carried out, for example, by initially producing the palladium(0), palladium (II), nickel(0), and/or nickel(II) compound in a dipolar-aprotic solvent or preparing said compound in situ in a dipolar-aprotic solvent, and then bringing it together with the secondary phosphine of the formula (VI), the base, the triflate compound, and optionally further solvent. It is also possible to prepare a mixture as described above that contains the palladium and/or nickel compound, to add this mixture to an initial charge of triflate compound, and then to add base, secondary phosphine of the formula (VI), and optionally further solvent. The preparation of the mixture containing palladium and/or nickel compounds can be carried out, for example, at −10 to +40° C., and the reaction with the triflate compound can be carried out at, for example, 20 to 160° C. The reaction of the triflate compound can require, for example, reaction times in the range from 5 to 200 hours.

Isolation and purification of the diphosphine compound of the formula (I) prepared in this way can be carried out, for example, by first stripping off the solvent at elevated temperature under reduced pressure, taking up the residue with toluene, passing this mixture over a silica column, taking the fraction containing the prepared diphosphine, stripping off the toluene therefrom, dissolving the residue in dimethylformamide, and crystallizing the prepared diphosphine by layering with methanol or dialkyl ether.

The present invention further relates to a process for the preparation of enantiomerically pure diphosphines of the formula (VIII)

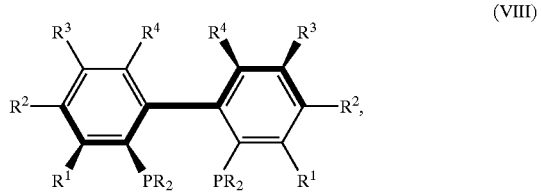

(VIII)

in which the symbols used have the meanings given for formula (I), and of a formula that is analogous to formula (VIII) but represents the other enantiomer.

This preparation is carried out according to the invention like the above-described preparation of the racemic diphosphines of the formula (I) and is additionally characterized in that the biphenyldiol of the formula (V) is subjected to racemate resolution. The racemate resolution can be carried out, for example, by crystallization using an auxiliary reagent or by chiral chromatography, e.g., according to the SMB method. Suitable auxiliary reagents for the racemate resolution by crystallization are, for example, tartaric acid derivatives and cinchonine derivatives.

For this purpose, preference is given to using (−)-O,O'-dibenzoyl-L-tartaric acid or enantiomerically pure N-benzylcinchonidinium chloride. Per mole of biphenyldiol, it is possible to use, for example, 0.5 to 1 mol of auxiliary reagent.

The racemate resolution can, for example be carried out by refluxing the racemic biphenyldiol of the formula (V) together with the auxiliary reagent in a suitable solvent, e.g., a C$_1$–C$_4$-alkyl alcohol or acetonitrile for a few hours, after-stirring, filtering off the precipitate that is present, and taking it up in a water-immiscible solvent (e.g., a chloroalkane, an aromatic hydrocarbon, or ethyl acetate), washing with an acid, e.g., a dilute mineral acid, separating off the organic phase, extracting the aqueous phase with a water-immiscible solvent, and stripping off the solvent from the combined organic phases.

The remaining preparation of enantiomerically pure diphosphines of the formula (VIII) is then carried out as described above for the preparation of racemic diphosphines.

The present invention further relates to enantiomerically pure diphosphines of the formula (IX)

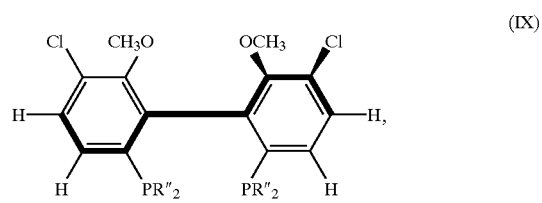

(IX)

in which the radicals R" are in each case identical and are 2-furyl, 2-N-methylpyrrolyl, 4-fluorophenyl, 3,5-dimethoxyphenyl, or 3,5-dimethylphenyl, and of a formula that is analogous to formula (IX) but represents the other enantiomer.

The present invention further relates to cycloheptadiene compounds of the formula (IV), to racemic and enantiomerically pure biphenyldiols of the formula (V), and to the corresponding racemic and enantiomerically pure triflate compounds accessible from the biphenyldiols of the formula (V), wherein in the triflate compounds in each case R$^1$ and R$^2$ are H, R$^3$ is chlorine, and R$^4$ is methoxy.

The racemic diphosphines of the formula (I) prepared according to the invention and the novel enantiomerically pure (+)- and (−)-diphosphines of the formula (VIII) are suitable as ligands for the preparation of catalysts, preferably of catalysts for hydrogenation. The enantiomerically pure (+)- and (−)-diphosphines of the formula (VIII) are particularly suitable as ligands for the preparation of hydrogenation catalysts for enantioselective hydrogenations.

Said ligands may, in order to be successful as hydrogenation catalysts, be combined with metals, including in the form of metal ions or metal complexes of elements of subgroup VIII of the Periodic Table of the Elements. In this connection, ruthenium, iridium, and rhodium are preferred. Here, the ligand-metal combination may be undertaken separately or in situ within the reaction mixture for the hydrogenation. In this connection, 0.5 to 10 mol (preferably 1 to 5 mol) of said ligands, for example, may be used per mole of metal.

The racemic diphosphines of the formula (I) can, for example, be used advantageously as ligands for palladium catalysts used in amination reactions. Numerous intermediates for pharmaceutical and crop protection active ingredients are accessible by palladium-complex-catalyzed aminations. It has hitherto been known to use binaphthylphosphorus compounds as ligands for such aminations.

Finally, the present invention also relates to catalysts that contain a metal, a metal ion or a metal complex of an element of subgroup VIII of the Periodic Table of the Elements and at least one diphosphine of the formula (IX). These catalysts preferably contain, independently of one another, ruthenium, iridium, or rhodium and 0.5 to 10 mol of a diphosphine of the formula (IX) per mole of metal, metal ion, or metal complex.

In the process according to the invention for the preparation of racemic diphosphines of the formula (I), it is advantageous that a broad palette of different ligands is accessible directly from one precursor (i.e., a compound of the formula (VI)). For example, it is readily possible to prepare different ligands, tailored to a specific catalyst problem, that have different electronic and steric ratios.

In the process according to the invention for the preparation of enantiomerically pure diphosphines of the formula (VIII), it is advantageous that the phosphine radicals are introduced only after the racemate resolution. As a result, it is possible to carry out the complex racemate resolution for diverse diphosphines in a common initial stage and only then prepare a broad spectrum of individual diphosphines. Separate racemate resolutions for individual diphosphines can thus be avoided.

The enantiomerically pure diphosphines of the formula (IX) according to the invention have the advantage that catalysts that can be prepared therefrom are superior to other catalysts in different reactions with regard to the enantiomer excess that is achievable following their use. Ruthenium catalysts with enantiomerically pure ligands according to the invention are, for example, advantageous for the enantioselective hydrogenation of heteroaromatic ketones and itaconic acid derivatives.

The cycloheptadiene compounds, biphenyldiols, and triflate compounds according to the invention are novel intermediates for the preparation of novel diphosphines, from which catalysts with superior properties can be prepared.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1
Preparation of Formaldehyde bis(4-chloro-3-methoxyphenyl)acetal (IUPAC: bis(4-chloro-3-methoxyphen-1-oxy)methane)

A solution of 100 g of 4-chloro-3-methoxyphenol in 250 ml of dimethylformamide was slowly added dropwise to a suspension of 16.0 g of sodium hydride (95% strength) in 300 ml of dimethylformamide under argon at 0° C. When the addition was complete, the mixture was after-stirred for a further 1 hour at 40° C., giving a clear, yellow solution. At room temperature, a solution of 88.1 g of diiodomethane in 100 ml of dimethylformamide was then slowly added dropwise. The solution was stirred for 15 hours at room temperature, during which an orange-red suspension gradually formed. The mixture was then stirred for a further 3 hours at 50° C. 400 ml of water were added and the mixture was extracted with 3×150 ml of methylene chloride. The combined organic phases were washed with 3×100 ml of saturated aqueous sodium chloride solution, the organic phases were dried over sodium sulfate, and the solvent was removed at 50° C. under reduced pressure, giving an orange-brown solid residue. This residue was dissolved in 250 ml of methyl tert-butyl ether at the boil, decanted off from the oily residue present and concentrated by evaporation until precipitation occurred. The mixture was left to crystallize first at room temperature and then, to complete the precipitation, at +40C. The precipitate was filtered off and carefully washed with 1:1 methyl tert-butyl ether/petroleum ether. The mother liquor was concentrated by evaporation and left to crystallize again.

Yield: 85.2 g (82% of theory)

Melting point: 110° C.

By removing the DMF prior to work-up with dichloromethane/water, it is possible to increase the chemical yield from 82 to 90%. The intensely colored phenol oxidation products that are present can be separated off by flash column chromatography over silica gel with dichloromethane as eluent.

$^1$H-NMR (CDCl$_3$): δ=3.87 (s, 6H, CH$_3$); 5.68 (s, 2H, CH$_2$); 6.65–6.70 (m, 4H, H$_{arom.}$); 7.27 (d, $^3J_{H-H}$=8.1 Hz, 2H, H$_{arom.}$)

$^{13}$C-NMR (CDCl$_3$): δ=56.2 (CH$_3$); 91.4 (CH$_2$); 102.0 (C$_{arom.}$); 108.2 (C$_{arom.}$); 116.2 (C$_{arom., ipso}$); 130.4 (C$_{arom.}$); 155.7 (C$_{arom., ipso}$); 156.5 (C$_{arom., ipso}$)

Example 2
Preparation of 2,10-dichloro-1,11-dimethoxy-5,7-dioxadibenzo[a,c]cycloheptadiene 239 ml of a 1.6 molar solution of butyllithium in hexane was slowly added dropwise to a solution of 60 g of formaldehyde [bis(4-chloro-3-methoxyphenyl)acetal] (IUPAC: bis(4-chloro-3-methoxyphen-1-oxy)-methane) in 100 ml of tetrahydrofuran at 0° C. under argon. When the addition was complete, the mixture was stirred for 15 hours at room temperature, giving a yellow suspension. The reaction mixture was then cooled to −50° C., and 51.3 g of anhydrous copper(II) chloride were added. The solution was then left to warm to room temperature over the course of 5 hours, and then 300 ml of water and 200 ml of methylene chloride were added. The mixture was neutralized with 50 ml of 2N aqueous hydrochloric acid, and then the resulting white-grey precipitate was redissolved by adding 300 ml of 25% strength aqueous ammonia solution. The methylene chloride phase was separated off and the deep dark-blue aqueous phase was further extracted with 5×100 ml of methylene chloride. The organic phase was then washed a few more times using a total of 400 ml of saturated aqueous ammonium chloride solution until it was only just still pale blue in color. The organic phase was concentrated somewhat by evaporation, dried over sodium sulfate, and all of the solvent was removed, giving a brown solid, which was treated with 100 ml of boiling methyl tert-butyl ether. The solution formed was decanted off from the oily residue and the solution was left to crystallize at +4° C. The solid that precipitated out was filtered off and the solvent was then removed from the filtrate under reduced pressure, and the residue that formed during this operation was subjected to column-chromatographic purification with silica gel 60 and with toluene as eluent. The yellow eluate was freed from the solvent under reduced pressure, and the residue was dissolved again in 40 ml of boiling methyl tert-butyl ether and left to crystallize at +4° C.

Yield: 45.4 g (77% of theory)

By drying the copper(II) chloride over $P_4O_{10}$ at 140° C. beforehand and by using an equimolar mixture of n-butyllithium and N,N,N,N-tetramethyl(ethylenediamine) (TMEDA) it is possible to achieve a very selective aromatic coupling to give the desired product (crude NMR shows only one product).

The removal of the THF prior to work-up and an acidic work-up with 4 N HCl has also proven advantageous.

The yield can be increased by these measures to 95% of theory.

Melting point: 130° C.

$^1$H-NMR (CDCl$_3$): δ=3.60 (s, 6H, OCH$_3$); 5.46 (s, 2H, OCH$_2$O); 6.94 (d, $^3J$=8.7 Hz, 2H, H$_{arom.}$); 7.43 (d, $^3J$=8.7 2H, H$_{arom.}$)

$^{13}$C-NMR (CDCl$_3$): δ=61.2 (CH$_3$); 102.3 (CH$_2$); 117.0 (C$_{arom.}$); 124.1 (C$_{arom., ipso}$); 124.9 (C$_{arom., ipso}$); 130.8 (C$_{arom.}$); 152.1 (C$_{arom., ipso}$); 154.4 (C$_{arom., ipso}$)

Example 3

Preparation of 5,5'-dichloro-6,6'-dimethoxybiphenyl-2,2'-diol 4 ml of concentrated aqueous hydrochloric acid were added to a suspension of 1.76 g of 2,10-dichloro-1,11-dimethoxy-5,7-dioxadibenzo-[a,c]cycloheptadiene in 25 ml of ethanol. The mixture was then refluxed under argon for 21 hours, the course of the reaction being monitored by means of thin-layer chromatography using methylene chloride as eluent. The resulting clear, yellow solution was admixed with 30 ml of water, extracted with 2×50 ml of methylene chloride, and washed with 2×50 ml of saturated aqueous sodium chloride solution. The organic phase was dried over sodium sulfate and filtered, and the solvent was removed under reduced pressure. The residue was carefully triturated with cold chloroform, which was decanted off again and discarded.

Yield: 1.54 g (91% of theory)

By adding 1.5 equivalents of ethylene glycol, based on the molar amount of the acetal used, the yield can be increased to 99% of theory.

Melting point: 110° C.

$^1$H-NMR (CDCl$_3$): δ=3.66 (s, 6H, OCH$_3$); 5.29 (s, 2H, OH); 6.84 (d, $^3J_{H—H}$=9.0 Hz, 2H, H$_{arom.}$); 7.37 (d, $^3J_{H—H}$=8.7 2H, H$_{arom.}$) $^{13}$C-NMR (CDCl$_3$): δ=61.1 (CH$_3$); 114.4 (C$_{arom.}$); 115.2 (C$_{arom. ipso}$); 119.1 (C$_{arom., ipso}$); 131.5 (C$_{arom.}$); 153.6 (C$_{arom., ipso}$); 153.8 (C$_{arom., ipso}$)

Example 4

Preparation of (+)-5,5'-dichloro-6,6'-dimethoxybiphenyl-2,2'-diol

A suspension of 22.9 g of 5,5'-dichloro-6,6'-dimethoxybiphenyl-2,2'-diol and 16.0 g of N-benzylcinchonidinium chloride in 110 ml of acetonitrile were refluxed for 4 hours and then stirred for 15 hours at room temperature. The resulting precipitate was filtered off, washed with a small amount of acetonitrile, and dried under reduced pressure. The residue was taken up in 250 ml of ethyl acetate and extracted by shaking with 2×50 ml of aqueous 2N hydrochloric acid. The organic phase was separated off, and the aqueous phase was extracted again with 2×50 ml of ethyl acetate. The combined organic phases were washed with 4×100 ml of saturated aqueous sodium chloride solution, dried over sodium sulfate, and filtered, and the solvent was removed under reduced pressure.

Yield: 6.77 g (30% of theory)

Enantiomer purity: 98.4 e.e.

The enantiomer purity was checked using analytical HPLC. The eluent used was n-heptane/isopropanol 80:20 [α]$_D$=+23.6 (c=1.5; CHCl$_3$)

Subsequent recrystallization from chloroform gave a product with an enantiomer purity of more than 99.9% e.e.

Example 5

Preparation of (5,5'-dichloro-6,6'-dimethoxybiphenyl-2,2'-diyl) bistrifluoromethanesulfonic acid ester 3.4 g of (+)-5,5'-dichloro-6,6'-dimethoxybiphenyl-2,2'-diol were suspended in 40 ml of toluene, and 2.5 g of pyridine were added, a clear, pale brown solution being formed within 10 min. A solution of 6.9 g of trifluoromethanesulfonic anhydride in 5 ml of toluene was added to this solution dropwise at room temperature. A flocculent precipitate formed rapidly. The mixture was stirred for 3 hours at 45° C., during which an orange-colored suspension was formed. This suspension was washed with 2×20 ml of water and then with 2×30 ml of saturated aqueous sodium chloride solution. The organic phase was dried over sodium sulfate and filtered, and the solvent was removed at 50° C. under reduced pressure, giving an orange-colored oil. This was pure enough to be further used directly. If desired, the oil could be further purified by flash column chromatography on silica gel with toluene as eluent.

Yield of oil: 5.7 g (92% of theory)

$^1$H-NMR (CDCl$_3$): δ=3.77 (s, 6H, OCH$_3$); 5.29 (s, 2H, OH); 7.18 (d, $^3J_{H—H}$=9.0 Hz, 2H, H$_{arom.}$); 7.58 (d, $^3J_{H—H}$=9.0 Hz, 2H, H$_{arom.}$)

$^{13}$C-NMR (CDCl$_3$): δ=61.5 (CH$_3$); 117.2 (C$_{arom.}$); 118.3 (q, $^1$J(C, F)=320 Hz, CF$_3$); 121.1 (C$_{arom. ipso}$); 127.8 (C$_{arom., ipso}$); 132.3 (C$_{arom.}$); 145.9 (C$_{arom., ipso}$); 155.9 (C$_{arom., ipso}$)

$^{19}$F-NMR (CDCl$_3$): δ=74.9 (s, CF$_3$)

Example 6

Preparation of (5,5'-dichloro-6,6'-dimethoxybiphenyl-2,2'-diyl)-bis(diphenylphosphine)

220 mg of Pd(PPh$_3$)$_4$ were added with 75 mg of diphenylphosphinopropane to 10 ml of dimethyl sulfoxide under argon, and the mixture was stirred for 3 hours at room temperature, during which time an orange-colored suspension formed. To this suspension were added 0.99 g of diphenylphosphine, 0.85 g of N,N-diisopropylethylamine, 1.00 g of (5,5'-dichloro-6,6'-dimethoxybiphenyl-2,2'-diyl)-bistrifluoromethanesulfonic acid ester, and a further 10 ml of dimethyl sulfoxide, and the clear, yellow solution was then stirred at 100° C. for 79 hours. When the reaction was complete, the solvent was removed under reduced pressure at 100° C., and 10 ml of methanol were added to the residue and left to crystallize at −25° C. The resulting fine precipitate was filtered off and washed with methanol.

Yield: 0.70 g (62% of theory).

The NMR data were identical to those given in EP-A 749,973.

Example 7

Preparation of (5,5'-dichloro-6,6'-dimethoxybiphenyl-2,2'-diyl)-bis(bis-2-furylphosphine)

100 mg of Pd$_2$(dibehzylideneacetone)$_3$ •CHCl$_3$ were suspended together with 80 mg of diphenylphosphinopropane in 10 ml of dimethylformamide under argon, and the mixture was stirred for 2 hours at room temperature, during which time a clear, orange-colored solution formed. This solution was transferred using a hollow needle to a Schlenk vessel, in which 3.40 g of (5,5'-dichloro-6,6'-dimethoxybiphenyl-2, 2'-diyl)-bistrifluoromethanesulfonic acid ester had been introduced. A further 10 ml of dimethylformamide, 1.56 g of triethylamine and 1.00 g of di-2-furylphosphine were added to this solution, and the mixture was stirred for 72 hours at 100° C., a further 1.03 g of bis-2-furylphosphine being added after 22 hours. When the reaction was complete, the solvent was removed under reduced pressure at 100° C., the residue was treated for one hour with 20 ml of diethyl ether in an ultrasound bath, and the ethereal solution was decanted off from the brown, oily residue. The ether was removed under reduced pressure, and the solid that remained was taken up in 2 ml of dimethylformamide, carefully covered with a layer of 10 ml of methanol, and left to crystallize at +4° C.

Yield: 0.85 g (24% of theory).
Melting point: 150° C.
$^1$H-NMR (CD$_3$CN): δ=3.28 (s, 6H, OCH$_3$); 6.37 (m, 2H, H$_{arom.}$); 6.44 (d, $^3J_{H—H}$=3.3 Hz, 2H, H$_{arom.}$); 6.48 (m, 2H, H$_{arom.}$); 6.65 (d, $^3J_{H—H}$=3.3 Hz, 2H, H$_{arom.}$); 7.44 (dt, $^3J_{H—H}$=8.1 Hz, $^3J_{H—H}$=8.1 Hz, $^3J_{H-P}$=1.5 Hz, 2H, H$_{arom.}$); 7.52 (d, $^3J_{H—H}$=8.4 Hz, 2H, H$_{arom.}$); 7.64 (d, $^3J_{H—H}$=1.8 Hz, 2H, H$_{arom.}$); 7.77 (d, $^3J_{H—H}$=1.8 Hz, 2H, H$_{arom.}$)
$^{13}$C-NMR (CDCl$_3$): δ=60.4 (CH$_3$); 110.6 (C$_{arom.}$); 110.8 (C$_{arom.}$); 121.4 (C$_{arom.}$); 121.8 (C$_{arom.}$); 129.2 (C$_{arom., ipso}$); 130.2 (C$_{arom.}$); 130.6 (C$_{arom.}$); 134.4 (C$_{arom., ipso}$); 136.7 (C$_{arom., ipso}$); 147.4 (C$_{arom.}$); 149.4 (C$_{arom. ipso}$); 150.2 (C$_{arom., ipso}$); 154.3 (C$_{arom., ipso}$)
$^{31}$P-NMR (CDCl$_3$) δ=−59.14

Repetition of this example using N,N-dimethylacetamide instead of dimethylformamide gave the same product in a reaction time of 12 hours.

Example 8

Preparation of (5,5'-dichloro-6,6'-dimethoxybiphenyl-2,2'-diyl)-bis(bis-p-fluorophenylphosphine)

100 mg of Pd$_2$(dibenzylideneacetone CHCl$_3$) were suspended together with 80 mg of diphenylphosphinopropane in 10 ml of dimethylformamide under argon, and the mixture was stirred for 2 hours at room temperature, during which time a clear, orange-colored solution formed. This solution was transferred using a hollow needle to a Schlenk vessel in which 3.28 g of (5,5'-dichloro-6,6'-dimethoxybiphenyl-2,2'-diyl)-bistrifluoromethanesulfonic acid ester had been introduced. To this solution were then added a further 10 ml of dimethylformamide, 1.50 g of triethylamine and 1.25 g of bis(p-fluorophenyl)phosphine, and then the mixture was stirred for 72 hours at 100° C., a further 1.75 g of bis-(p-fluorophenyl)phosphine being added after 23 hours. When the reaction was complete, the solvent was removed under reduced pressure at 100° C., the residue was treated for one hour with 10 ml of diethyl ether in an ultrasound bath, and the solution was decanted off from the brown, oily residue. The ether was removed under reduced pressure, and the residue was taken up in 2 ml of dimethylformamide, carefully coated with a layer of 10 ml of methanol, and left to crystallize at +4° C.

Yield: 0.80 g (20% of theory).
Melting point: 139° C.
$^1$H-NMR (CD$_3$CN): δ=3.35 (s, 6H, OCH$_3$); 6.88–7.13 (m, 14H, H$_{arom.}$); 7.16–7.27 (m, 4H, H$_{arom.}$); 7.46 (d, $^3J_{H—H}$=8.1 Hz, 2H, H$_{arom.}$)
$^{13}$C-NMR (CDCl$_3$): δ=60.2 (CH$_3$); 115.5 (C$_{arom.}$); 115.8 (C$_{arom.}$); 128.7 (C$_{arom.,ipso}$); 130.2 (C$_{arom.}$); 130.7 (C$_{arom.}$); 131.7 (C$_{arom.,ipso}$); 132.7 (C$_{arom.,ipso}$); 134.6 (C$_{arom.}$); 136.2 (C$_{arom.}$); 137.8 (C$_{arom., ipso}$); 154.3 (C$_{arom., ipso}$); 161.4 (C$_{arom.,ipso}$); 161.9 (C$_{arom. ipso}$); 164.7 (C$_{arom., ipso}$); 165.2 (C$_{arom, ipso}$)
$^{31}$P-NMR (CDCl$_3$) δ=−16.01
$^{19}$F-NMR (CDCl$_3$) δ=113.6 (s, Ar—F); −112.3 (s, Ar—F)

Example 9

Preparation of (5,5'-dichloro-6,6'-dimethoxybiphenyl-2,2'-diyl)-bis(bis-3,5-dimethylphenylphosphine)

100 mg of Pd$_2$(dibenzylideneacetone)$_3$ CHCl$_3$ were suspended together with 80 mg of diphenylphosphinopropane in 10 ml of dimethylformamide under argon, and the mixture was stirred for 1 hour at room temperature, during which time a clear orange-colored solution was formed. This solution was transferred using a hollow needle to a Schlenk vessel into which 2.70 g of (5,5'-dichloro-6,6'-dimethoxybiphenyl-2,2'-diyl)bistrifluoromethanesulfonic acid ester had been introduced. To this solution were added a further 10 ml of dimethylformamide, 1.60 g of N,N-diisopropylethylamine, and 2.43 g of bis-(3,5-dimethylphenyl)phosphine, and then the mixture was stirred for a total of 115 hours at 100° C., a further 0.25 g of bis-(3,5-dimethylphenyl)phosphine being added after 75 hours, and a further 0.32 g of bis-(3,5-dimethylphenyl) phosphine being added after 100 hours. When the reaction was complete, the dimethylformamide was removed under reduced pressure at 100° C., and the residue was subjected to flash column chromatography over silica gel 60 using toluene as eluent. The solvent was removed under reduced pressure, and the residue was taken up in 2 ml of dimethylformamide, carefully coated with a layer of 8 ml of methanol, and left to crystallize at +4° C. Following removal of the 1st precipitation fraction, the filtrate was concentrated to 1 ml at 100° C. and, again after coating with methanol, left to crystallize.

Yield: 1.50 g (42% of theory).
Melting point: 225° C.
$^1$H-NMR (CD$_3$CN): δ=2.14 (s, 12H, Ar—CH$_3$); 2.22 (s, 12H, Ar—CH$_3$); 3.27 (s, 6H, OCH$_3$); 6.80–6.90 (m, 12H, H$_{arom.}$); 6.99 (d, $^3J_{H—H}$=9.0 Hz, 2H, H$_{arom.}$); 7.31 (d, $^3J_{H—H}$=9.0 Hz, 2H, H$_{arom.}$)
$^{31}$P-NMR (CDCl$_3$): δ=−n13.73

Example 10-1

Preparation of (5,5'-dichloro-6,6'-dimethoxybiphenyl-2,2'-diyl)-bis(bis-2-(-N-methylpyrrolyl)phosphine)

a) Preparation of di(N-methylpyrrolyl)ethyl phosphinite

To a solution of 38.61 g of methylpyrrole in 200 ml of diethyl ether were added dropwise, at 0° C., first 297.5 ml of a 1.6 molar solution of n-butyllithium in hexane and then 35.0 g of dichloroethyl phosphinite. The reaction solution was then stirred overnight at room temperature, and then the solvent was stripped off under reduced pressure. The residue that remained was taken up in 200 ml of petroleum ether, the insoluble lithium salts were filtered off, and the solvent was stripped off from the filtrate. The residue that was formed during this operation was fractionally distilled.

Yield: 14.14 g (25% of theory).
Boiling point: 125–130° C. at 0.17 torr.
$^{31}$P-NMR shift: 76.54 ppm in CDCl$_3$ b) Preparation of di-2-(N-methylpyrrolyl)-phosphine To a suspension of 0.75 g of lithium aluminum hydride in 20 ml of tetrahydrofuran were added dropwise, at −70° C., 2.15 g of trimethylchlorosilane, and the suspension was then stirred for 2 hours at room temperature. A solution of 2.15 g of di(N-methylpyrrolyl)ethyl phosphinite in 10 ml of tetrahydrofuran was then added dropwise. The reaction mixture was stirred for 20 hours at room temperature. The reaction mixture was then hydrolyzed with 1 g of water (until there was no further evolution of hydrogen), the solvent was stripped off under reduced pressure, and the residue that remained was taken up in petroleum ether. After the insoluble aluminum and lithium salts had been filtered off, the solvent was stripped off from the filtrate and the residue that formed during this operation was dried under reduced pressure.

Yield: 30% of theory.

$^{31}$P-NMR shift: −111.36 ppm in $C_6D_6$ c) Synthesis of the Compound Stated at the Outset The procedure was as described in Example 6, but using di-2-(N-methylpyrrolyl)phosphine instead of diphenylphosphine. $^1$H-NMR (CDCl$_3$): δ=3.04 (s, 6H); 3.26 (s, 6H); 3.66 (s, 6H); 5.98–6.01 (m, 2H); 6.65 (t, 2H); 6.07–6.1 (m, 2H); 6.17 (t, 2H); 6.65 (t, 2H); 6.84–6.87 (m, 2H); 6.88–6.93 (m, 2H); 7.3 (d, 2H)

$^{31}$P-NMR (CDCl$_3$): δ=−58.75

Example 10-2

Preparation of (5,5'-dichloro-6,6'-dimethoxybiphenyl-2,2'-diyl)-bis(bis-3,5-dimethoxyphenyl)phosphine)

In a heat-dried Schlenk vessel with a Teflon stirrer bar, 26.4 mg of [Pd$_2$(dba)$_3$]•CHCl$_3$ and 1.1 mg of diphenylphosphinopropane were suspended in 3 ml of dimethylacetamide, and the mixture was stirred for 30 min at room temperature, during which operation the solution became clear and assumed a red color. This solution was transferred using a hollow needle into a Schlenk vessel in which 0.95 g of (5,5'-dichloro-6,6'-dimethoxybiphenyl-2,2'-diyl)-bistrifluoromethanesulfonic acid ester and 1.1 g of bis(3,5-dimethoxyphenyl)phosphine in 10 ml of dimethylacetamide had been introduced. 0.64 g of diisopropylethylamine were then added and the mixture was heated to 80° C. After 72 hours, the solvent was removed under reduced pressure, and the residue was taken up in 2 ml of toluene and purified using flash-chromatography over silica gel with toluene as eluent. The yellowish oil that formed was taken up in diethyl ether, and the ether was then removed under reduced pressure. This gave 0.78 g of the product as a pale yellow voluminous substance.

Yield: 53% of theory $^{31}$P-NMR-(CDCl$_3$): δ=−10.61 MS (SIMS): m/z (%)= 890.9 (9, M$^+$), 753.0 (5, M$^+$—C$_8$H$_{10}$O$_2$), 584.9 [100, M$^+$—P(C$_8$H$_{10}$O$_2$)$_2$], 448.9 [2, M$^+$—P(C$_8$H$_{10}$O$_2$)$_2$—C$_8$H$_{10}$O$_2$], 384.9 3, 337.0 5, 280.9 {19, M$^+$—[P(C$_8$H$_{10}$O$_2$)$_2$]$_2$} 220.9 (28), 206.9 (33), 146.9 (70).

Example 11

Preparation of the Catalyst (5,5'-dichloro-6,6'-dimethoxybiphenyl-2,2'-diyl)-bis(di-3,5-dimethylphenylphosphino)-bis(3,3,3-trifluoroaceto)ruthenium 0.0431 g of (cyclooctadiene)Ru(π$^3$-methallyl)$_2$ and 0.1033 g of (5,5'-dichloro-6,6'-dimethoxybiphenyl-2,2'-diyl)-bis(bis-3,5-dimethylphenylphosphine) were dissolved in 5 ml of methylene chloride, 5 ml of methanol were added, and then, with stirring, 21.5 μl of trifluoroacetic acid were added. After the mixture had been stirred for 24 hours at room temperature, the solvent was removed under reduced pressure and the orange-colored residue was dried for 2 hours under reduced pressure.

Example 12

Preparation of the Catalyst (5,5'-dichloro-6,6'-dimethoxybiphenyl-2,2'-diyl)bis(bis-4-fluorophenylphosphino)-bis(3,3,3-trifluoroaceto)ruthenium The preparation was as described in Example 11, but now using the corresponding bis-4-fluorophenylphosphine instead of (5,5'-dichloro-6,6'-dimethoxybiphenyl-2,2'-diyl)-bis(bis-3,5-dimethylphenylphosphine).

Example 13-1

Preparation of the catalyst (5,5'-dichloro-6,6'-dimethoxybiphenyl-2,2'-diyl)-bis(di-2-furylphosphino)-bis(3,3,3-trifluoroaceto)ruthenium The preparation was as described in Example 11, but now using the corresponding bis-2-furylphosphine instead of (5,5'-dichloro-6,6'-dimethoxybiphenyl-2,2'-diyl)-bis(bis-3,5-dimethylphenylphosphine).

Example 13-2

Preparation of the Catalyst (5,5'-dichloro-6,6'-dimethoxybiphenyl-2,2'-diyl)-bis(3,5-dimethoxyphenylphosphino)-bis(3,3,3-trifluoroaceto) ruthenium 432 mg of the product from Example 10-2 were added to a solution of 155 mg of (cyclooctadiene)Ru(π$^3$-methallyl)$_2$ in CH$_2$Cl$_2$, and the mixture was stirred for 1 hour at room temperature. The solvent was then removed under reduced pressure. The product was formed as a dark green solid in quantitative yield.

$^{31}$P-NMR-(d$^4$-MeOH): δ=64.22

MS (SIMS): m/z (%)=1143.2, 991.2 [12, M$^+$—(CO$_2$CF$_3$)$_2$], 585.3 [M$^+$—Ru(CO$_2$CF$_3$)$_2$—P(C$_8$H$_{10}$O$_2$)$_2$], 147.1 (19), 132.9 (28), 73.1 (100).

Examples 14 to 20

Hydrogenations with Catalysts from Examples 11 to 13.

20 μmol of catalyst were dissolved in 5 ml of methanol, 2.0 ml of dimethyl itaconate, and 0.100 g of diglyme (GC standard) were added, and the mixture was reacted with hydrogen in a glass autoclave (1 bar of H$_2$) or steel autoclave (70 bar of H$_2$). When the reaction period had expired, and optionally following decompression, a vacuum was applied to remove dissolved hydrogen, and the catalyst/product solution was then analyzed by gas chromatography. The results are summarized in Table 1.

TABLE 1

| Example | Catalyst from Example | Temp. (° C.) | Pressure (bar) | Reaction time (h) | Conversion (%) | Yield (%) | TOF/h$^{-1}$ | ee (%) | Configuration |
|---|---|---|---|---|---|---|---|---|---|
| 14 | 13-1 | 23 | 70 | 15 | 99.9 | 100 | 6.6 | 65.5 | (S) |
| 15 | 13-1 | 50 | 1 | 1 | 17.0 | 12.2 | 12.3 | 92.5 | (S) |
| 16 | 12 | 22 | 1 | 1 | 70 | 71 | 70 | 94.7 | (S) |
| 17 | 12 | 22 | 1 | 0.7 | 35 | 34 | 49.8 | 96.2 | (S) |
| 18 | 12 | 50 | 1 | 0.5 | 100 | 100 | 198 | 95.5 | (S) |
| 19 | 11 | 22 | 1 | 1 | 100 | 100 | 22 | 94.7 | (S) |
| 20 | 11 | 50 | 1 | 0.5 | 100 | 100 | >200 | 96.9 | (S) |

Examples 21 to 24

Hydrogenations with In situ Catalyst Systems

20 µmol of (norbornadiene)$_2$RhPF$_6$ were dissolved with in each case 20 mmol of the ligands from Examples 7 to 9 in 5 ml of a solvent. When using the ligand from Example 7, the solvent was methanol, and when using the ligands from Examples 8 and 9, the solvent was a 1:1 mixture of methylene chloride and methanol. The mixture obtained was stirred for 1 hour at 40° C., then the solvent was removed under reduced pressure, and then 5 ml of methanol were added. 2.0 mmol of dimethyl itaconate and 0.100 g of diglyme (GC standard) were added, and the mixture was reacted with hydrogen in a glass autoclave (1 bar of H$_2$) or steel autoclave (70 bar of H$_2$). After the reaction time had expired, and optionally after decompression, a vacuum was applied to remove dissolved hydrogen, and the catalyst/product solution was then analysed using gas chromatography. The results are summarized in Table 2.

TABLE 2

| Example | Ligand | Temp. (° C.) | Pressure (bar) | Reaction time (h) | Conversion (%) | Yield (%) | TOF/h$^{-1}$ | ee (%) | Configuration |
|---|---|---|---|---|---|---|---|---|---|
| 21 | from Example 7 | 24 | 1 | 1 | 95 | 100 | 120 | 31.4 | (S) |
| 22 | from Example 7 | 22 | 70 | 0.5 | 97 | 95 | 193 | 14.3 | (S) |
| 23 | from Example 8 | 22 | 1 | 1 | 12 | 16 | 22 | 26 | (S) |
| 24a) | from Example 9 | 22 | 1 | 1 | 100 | 100 | 98.5 | 78.3 | (S) |
| 24b) | from Example 9 | 22 | 100 | 0.5 | 100 | 100 | 196 | 58.5 | (S) |
| 24c) | from Example 9 | 50 | 100 | 0.5 | 100 | 100 | >200 | 74.2 | (S) |

Examples 25 to 28

Hydrogenations with the Catalyst from Example 13-2

In a heat-dried glass autoclave (a steel autoclave was used in Example 27) charged with argon, a solution of 0.32 g of dimethyl itaconate, 0.024 g of the catalyst from Example 13-2, 0.1 g of diglyme, and 5 ml of methanol was added and then 1 bar (in Example 27 70 bar) of hydrogen was fed in. Then, at the temperature given in Table 3, the mixture was vigorously stirred for 30 min. Then, to remove the hydrogen, a sample was taken to determine the conversion (GC), the mixture that remained was subjected to flash distillation, and the enantiomer excess in the distillate was determined.

In Example 28, 0.64 g of dimethyl itaconate were used. Details are given in Table 3.

TABLE 3

| Example | Temp. (° C.) | Pressure (bar) | Conversion (%) | TOF/h$^{-1}$ | ee (%) |
|---|---|---|---|---|---|
| 25 | 22 | 1 | 99.9 | 138 | 92.4 |
| 26 | 40 | 1 | 99.7 | >200 | 92.4 |
| 27 | 22 | 70 | 99.7 | >200 | 55.6 |
| 28 | 22 | 1 | 38.3 | 136 | 91.2 |

What is claimed is:

1. Enantiomerically pure diphosphines of the formula (IX)

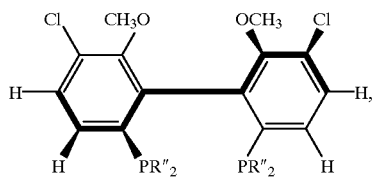

(IX)

and enatiomerically pure enantiomers thereof, in which the radicals R" each case identical and are 2-furyl, 2-N-methylpyrrolyl, and 4-fluorophenyl.

* * * * *